United States Patent [19]
Shioguchi et al.

[11] Patent Number: 5,883,274
[45] Date of Patent: Mar. 16, 1999

[54] PROCESS OF MEASURING CLOUD POINT OF POLYGLYCEROL-FATTY ACID ESTER, PROCESS OF EVALUATING PROPERTIES THEREOF, AND PROCESS OF PRODUCING THEREOF USING THE SAME

[75] Inventors: Kaoru Shioguchi, Ayase; Hiroshi Kuzui, Fuchu; Akifumi Yuuki, Tokorozawa, all of Japan

[73] Assignee: Mitsubishi Chemical Corporation, Tokyo, Japan

[21] Appl. No.: 665,646

[22] Filed: Jun. 18, 1996

[30] Foreign Application Priority Data

Jun. 19, 1995 [JP] Japan ..................................... 7-173943
Oct. 5, 1995 [JP] Japan ..................................... 7-282409

[51] Int. Cl.$^6$ ............................ C07C 53/00; C07C 51/00
[52] U.S. Cl. ........................................... 554/227; 554/124
[58] Field of Search ...................................... 554/124, 227

[56] References Cited

U.S. PATENT DOCUMENTS 4,597,906  7/1986  Uhrig et al. ............................. 260/401
4,695,411  9/1987  Stern et al. ............................ 269/410.9
5,160,450  11/1992  Okahara et al. .................... 252/174.21

OTHER PUBLICATIONS

Ca—"Solution Properties of Homogeneous Polyglycerol Dodecyl Ether Nonionic Surfactants" Jacos, vol. 66, No. 1 (Jan. 1989).

*Primary Examiner*—Jose G. Dees
*Assistant Examiner*—Alton Pryor
*Attorney, Agent, or Firm*—David G. Conlin; David S. Resnick; Dike, Bronstein, Roberts & Cushman, LLP

[57] ABSTRACT

The present invention relates to a process of measuring a cloud point of polyglycerol-fatty acid ester comprising;

adding polyglycerol-fatty acid ester to an aqueous solution of a salt, a polyhydric alcohol, or a mixture thereof to prepare a homogeneous aqueous polyglycerol-fatty acid ester solution;

heating the obtained homogeneous aqueous solution to allow to change the homogeneous aqueous solution into a heterogeneous aqueous solution; and measuring a temperature at which the homogeneous aqueous solution changes into the heterogeneous aqueous solution.

22 Claims, No Drawings

PROCESS OF MEASURING CLOUD POINT OF POLYGLYCEROL-FATTY ACID ESTER, PROCESS OF EVALUATING PROPERTIES THEREOF, AND PROCESS OF PRODUCING THEREOF USING THE SAME

BACKGROUND OF THE INVENTION

This invention relates to a process for measuring a cloud point of polyglycerol-fatty acid ester, a process for evaluating properties of the polyglycerol-fatty acid ester based on the results of the cloud point measurement, and a process for producing the polyglycerol-fatty acid ester using the above-mentioned processes.

Polyglycerol-fatty acid esters (hereinafter referred to as "PGE") are widely utilized as surfactants or emulsifying agents for foods, medicines, cosmetics, or the like. A ratio of a hydrophilic moiety to a lipophilic moiety in the PGE, namely a hydrophilic-lipophilic balance (hereinafter referred to as "HLB") is one of important factors for determining a surface activity of the PGE, when the PGE is mainly used as surfactants. The HLB of the PGE is adjusted by controlling the degree of polymerization of polyglycerol (hereinafter referred to as "PG") or selecting a suitable feed ratio of raw materials for controlling an amount of fatty acid ester (average esterification degree) bonded to a hydroxyl group of the PG.

The PGE is mainly produced by esterifying the PG obtained by the polycondesation of glycerol with fatty acid or derivatives thereof in the presence of an alkaline catalyst. The esterified product (PGE) is used as surfactants or the like, directly after the production or after simple purification treatments in which coloring or odor components are removed from the product, for example, by stream distillation.

In order to produce the PGE having a required HLB and average esterification degree, the production conditions are adequately selected in the following manner, that is, PG and fatty acid fed at a particular ratio are first reacted to obtain the PGE. The resultant PGE is then analyzed to determine the esterification degree of the PGE and to simultaneously ascertain whether the PGE exhibits properties such as a surface activity similar to those of an aimed PGE. Accordingly, if the PGE produced differs from the aimed PGE, a number of experiments or tests must be repeated to optimize the reaction conditions including the feed ratio of the fatty acid to PG, the reaction time, the reaction temperature, the amount of the catalyst used, or the like and it takes much time to determine the production condition.

Conventionally, there have been used various chemical analyzing methods for determining properties of the PGE. For example, in order to evaluate the esterification degree and the amount of residual fatty acid, the measurements of acid value, ester value and hydroxyl number of PGE has been used. Further, various evaluation methods such as an analysis of ignition residues has been used to determine amounts of soap and residual catalyst.

However, the PG skeleton which is hydrophilic moiety of PGE is a polycondensate of glycerol and therefore exhibits a particular distribution of degree of polymerization thereof. In addition, the PGE contains not only linear polymers but also branched or cyclic polymers. Since the viscosity of PG generally increases so that the degree of polymerization thereof becomes larger, it becomes extremely difficult to purify the PG by separating the cyclic polymers or the like from the polycondensate. As a result, the PGE which is a reaction product obtained by esterifying hydroxyl groups of the PG with fatty acid, is a mixture composed of the PGEs having different PG skeletons and various esterification degrees, and unreacted PG.

Also, the PGE as the esterified product contains soaps as a by-product produced by the reaction of the alkaline catalyst with raw fatty acid, or unreacted fatty acid which is remained in case where the insufficiently esterification reaction of the PG and the fatty acid is carried out or in case where fatty acids are used in an excess amount relative to a stoichiometric amount thereof.

Thus, since the PGE produced comprises a mixture having a complicated composition, even though the PGEs exhibit similar or same esterification degrees, respectively, the properties such as emulsifying stability of the PGEs may be quite different from each other. As a result, by conventional chemical analyzing methods used for determining average esterification degrees and the amount of unreacted PG, the properties of the PGE produced cannot be evaluated sufficiently.

On the other hand, there have been used another type of evaluation methods for surfactants, by using the properties of the surfactants measured directly. For example, there is known a method for measuring a cloud point of an aqueous solution of a polyoxyethylene-based nonionic surfactant produced from ethylene oxide ("Dictionary of Technical Terms for Fats and Oils" (Saiwai Shobo)). Generally, the "cloud point" in surfactants is determined as a temperature at which an aqueous solution of the nonionic surfactant is separated into two phases with a rise of temperature. Such separated two phases can return to homogeneous phase with a decline of temperature.

In the polyoxyethylene-based surfactants, there is known a correlation in the range of the cloud point and an average degree of polymerization of the polyoxyethylene chain. The cloud point of the polyoxyethylene-based surfactant is increased depending on the increase of average degree of polymerization of the polyoxyethylene. Hence, in order to produce an aimed surfactant, the reaction conditions is adjusted such that the degree of addition polymerization of ethylene oxide is present in an adequate range. Such an adjustment of the reaction conditions is achievable only in the case where a hydrophilicity of an ether group-existing in polyoxyethylene of the surfactant become poor with a rise of temperature.

On the other hand, in the case of the PGE, since a hydrophilic moiety thereof is a polycondensate of glycerol and is different from the polyoxyethylene chain of the above-mentioned surfactant, not only a hydroxyl group and an ether group coexist in the PGE but also the PGE has an extremely complicated composition caused by a branched-chain condensation and cyclic polycondensation due to the existence of the hydroxyl group.

As a result of earnest studies by the present inventors on evaluation process of properties of the PGE, it has been found that under a particular condition, the PGE has a cloud point similar to the known cloud point of the polyoxyethylene-based surfactant, and the cloud point of the PGE can be measured at a temperature of 0° to 100° C. by preparing a homogeneous aqueous PGE solution thereof to which a salt and/or polyhydric alcohol are added a PGE solution. On the basis of these findings, the present invention has been attained.

SUMMARY OF THE INVENTION

The objects of the present invention is to provide a process for measuring a cloud point of PGE, a process for evaluating properties of the PGE based on the results of the cloud point measurement and a process for producing the PGE using the above-mentioned processes.

To accomplish the aims, in a first aspect of the present invention, there is provided a process for measuring a cloud point of PGE, comprising adding PGE to an aqueous solution of a salt, a polyhydric alcohol, or a mixture thereof to prepare a homogeneous aqueous PGE solution, heating the obtained homogeneous aqueous PGE solution to allow to change the homogeneous aqueous solution into a heterogeneous aqueous PGE solution, and measuring a temperature at which the homogeneous aqueous solution changes into the heterogeneous aqueous solution.

In a second aspect of the present invention, there is provided a process of evaluating PGE properties, comprising measuring cloud points of a reference PGE and an aimed PGE at different concentrations of a salt, polyhydric alcohol or a mixture thereof according to the first aspect, preparing a profile indicating a relationship in the range of each measured cloud point and the concentration of the salt, (hereinafter referred to as "cloud point profile"), and comparing the cloud point profile for the reference PGE with the profile for the aimed PGE.

In a third aspect of the present invention, there is provided a process of the preparation of PGE, comprising measuring cloud points of the reference PGE and aimed PGE at different concentrations of a salt, polyhydric alcohol or a mixture thereof according to the first aspect, preparing each cloud point profile for the reference PGE and aimed PGE, comparing each cloud point profile for the aimed PGE with the cloud point profile for the reference PGE, adjusting reaction conditions for the production of the aimed PGE based on deviation of the profile for the aimed PGE from the profile for the reference PGE, and producing PGE under the adjusting reaction condition.

DETAILED DESCRIPTION OF THE INVENTION

The present invention is described in detail below.

The processes according to the present invention can be applicable to any kind of PGEs. Especially, hydrophilic PGEs which is easily dispersed or dissolved in cold water containing no salt nor polyhydric alcohol, are preferably used in the present invention because the cloud point of the PGE can be easily measured. The hydrophilic PGEs include, for example, those prepared by reacting the fatty acid and the PG at a feed molar ratio of the fatty acid to the PG of not more than 5.

The PG as a raw material for the PGE can be produced according to any known methods thereof. In general, the process comprises adding acidic or alkaline catalyst to glycerol in a small amount, and heating the reaction system at a temperature of not less than 180° C. under atmospheric or reduced pressure. After the reaction, the resultant PG is subjected to neutralization or desalting treatment, if necessary. The PG used in the present invention can have an optional average degree of polymerization without limitation. Generally, the average degree of polymerization of the PG is 4–30. When the PGE which is an esterified product of the PG, is used as additives for foods or the like, the average degree of polymerization of the PG is preferably in the range of 4 to 20, more preferably 6 to 12.

The fatty acid which is reacted with the PG to obtain the PGE, may include free fatty acids or esters of such fatty acids with lower alcohols. Any kind of fatty acids can be used for the preparation of the PGE. In general, linear or branched, saturated or unsaturated $C_6$–$C_{22}$ fatty acids or $C_6$–$C_{22}$ hydroxy-containing fatty acids are preferable. The fatty acids can be used singly or in the form of a mixture containing 2 or more of the fatty acids at optional mixing ratios. Examples of the preferable fatty acids include capric acid, caprylic acid, lauric acid, myristic acid, palmitic acid, stearic acid, oleic acid, ricinoleic acid, iso-stearic acid, hydroxy-stearic acid, 2-ethyl-hexanoic acid, behenic acid, erucic acid, or lower alkyl esters of these fatty acids including methyl esters, ethyl esters or glycerol esters. These example of the fatty acids can be used as a single or mixture of two or more.

The PGE can be prepared by the esterification with the PG and the fatty acid or by esterexchange reaction with the PG and a fatty acid ester. The esterification or esterexchange reaction is generally carried out at an elevated temperature of not less than 130° C. in the presence of an alkaline catalyst. The reaction system may be either reduced pressure system or atmospheric pressure system. If necessary, after the reaction, the neutralization or desalting is carried out for the reaction product. Similarly, the esterification or esterexchange reaction can be carried out in the presence of enzymes such as lipase. As the PGE usable in the present invention, there may be exemplified the obtained crude PGE containing unreacted PG, by-product or the like, and PGE subjected to purification treatment such as stream distillation to remove colored or odor components. Further, the mixed PGE containing the another PGEs prepared under different reaction conditions at an adequate mixing ratios may be exemplified.

The cloud point measured in the present invention means a temperature at which a homogeneous phase aqueous solution of the PGE to which the salt and/or the polyhydric alcohol are added, is changed to a heterogeneous phase aqueous solution of PGE with the rise of temperature.

Here, the homogeneous phase aqueous solution in the present invention means a solution which does not undergo any change in phase state (such as phase separation, generation or adhesion of oil drops, or the like) even after the PGE-containing solution has been allowed to stand for 30 minutes under the conditions in which the measurement is carried out. The homogeneous phase aqueous solution includes an emulsion and a dispersion. On the other hand, the heterogeneous phase aqueous solution in the present invention means a solution completely separated into two phases, namely a PGE phase and a water phase, or a solution containing oil drops. The separated PGE phase is in the form of an oily or gelled phase clearly divided from the remainder of the solution composed of the translucent water phase. However, the heterogeneous phase aqueous solution does not include emulsion and dispersion.

The solution used for the measurement of cloud point in the present invention, is specifically prepared in the following manner. First, a salt is added to desalted water and agitated or stirred, if necessary while heating, to prepare an aqueous solution of the salt. The aqueous salt solution thus obtained is then added to PGE in a sealed bottle. The sealed bottle is agitated or stirred, if necessary while heating, to prepare a homogeneous phase aqueous solution containing the PGE. At this time, when the solution is heated to a temperature not less than a melting point of the PGE, it is easy to dissolve the PGE in the solution. The resultant homogeneous phase aqueous solution containing the PGE is shaken or agitated and then allowed to stand at a temperature of 0° to 100° C. to measure a cloud point thereof.

More specifically, a sample of the homogeneous phase aqueous solution containing the PGE is first charged into a transparent bottle made of glass or the like. The transparent bottle is dipped in a thermostatic bath whose temperature is kept constant, to observe whether any phase separation of the solution is caused. If any phase separation occurs in the solution, it is considered that a cloud point of the liquid sample exists at not more than the given measuring temperature. When the above-mentioned procedure is repeated given times or when the measurements are carried out at various temperatures, the cloud point of the solution or the range therefor can be determined. Further, in case where the cloud point measurement is performed at predetermined intervals of temperature, the cloud point is determined as an intermediate value between an upper temperature at which a phase separation is observed and a lower temperature immediately below the upper temperature, at which the phase separation has not yet been caused.

From an industrial viewpoint, it is possible that the cloud point is measured at a temperature interval of not more than 1° C. However, considering a complicated operation and an accuracy of the measurement, the temperature interval may be practically 2° to 5° C. In a certain case, the temperature interval about 10° C. Namely, in the present invention, the temperature interval of not more than 10° C. can be adopted.

The cloud point is generally measured in the range of 0° C. to 100° C. If the measuring temperature is out of the above-mentioned range, that is, less than 0° C. (less than a melting point of water) or more than 100° C. (more than a boiling point of water), the measurement of cloud point may be inaccurate because it is difficult to observe the phase state.

A lower limit of the measurable temperature of cloud point usable is determined by a melting point of an aimed PGE. If the measuring temperature is below the melting point of the PGE, it may be difficult to measure the cloud point of the aimed PGE because a viscosity of the aqueous PGE-containing solution to be measured is increased due to solidification of the PGE, so that the aqueous solution becomes gel state. The melting point of the PGE is primarily determined by a kind of the fatty acid moiety constituting the PGE. In general, if the fatty acid moiety comprises saturated fatty acid having not less than 16 carbon atoms, the lower limit of the measurable temperature of cloud point is about 50° C. On the other hand, if the fatty acid moiety comprises saturated fatty acid having not more than 12 carbon atoms, the lower limit of the measurable temperature of cloud point is 0° C. Further, if the fatty acid moiety comprises unsaturated fatty acid, the lower limit of the measurable temperature of cloud point is also 0° C.

In order to measure the cloud point of the PGE in the above-mentioned range of 0° C. to 100° C., the salt and/or polyhydric alcohol are added to the aqueous solution thereof, depending upon a kind of PGE to be measured. In this case, by properly selecting a kind or a mixing ratio of the salt and/or polyhydric alcohol added, the cloud point of the PGE can be adjusted in the range of 0° C. to 100° C., whereby it becomes possible to practically measure the cloud point of the PGE. Thus, the salt is added to the aqueous solution to decrease the cloud point of the aqueous PGE solution. Examples of the salts used for decreasing the cloud point of the aqueous PGE solution, may include nitrates such as sodium nitrate, bromides such as sodium bromide, chlorides such as sodium chloride, calcium chloride or aluminum chloride, sulfates such as lithium sulfate or sodium sulfate, citrates such as sodium citrate or potassium citrate, or the like. The preferred salt added to the aqueous PGE solution are inorganic salts, especially an alkali metal salt of an inorganic acid. The effect of decreasing the cloud point of the aqueous PGE solution, varies depending upon the kind of the salt added. Consequently, the salt may be properly selected depending upon a melting point of the PGE. When an aqueous solution of the PGE is subjected to the measurement of its cloud point, a suitable concentration of the salt added can be determined by a preliminary conducted experiments. The concentration of the salt added in the present invention is determined by weight of salts to total weight of salts, polyhydric alcohol and water not including PGE. The concentration of the salt added varies depending upon the kind thereof, and is generally in the range of 0 to 50% by weight, preferably 0 to 30% by weight. If the concentration of the salt is more than 50% by weight, the concentration of the salt exceeds the saturated solubility of the salt to water and may be unpreferable. The effect of decreasing the cloud point of the aqueous PGE solution by the addition of the salt is based on the same effect as salting-out of protein by the addition of salt. It is suggested that an intensity of the effect of decreasing the cloud point is due to lyotropic series.

By the addition of the polyhydric alcohol to the aqueous PGE solution, the cloud point thereof is rised. The preferable polyhydric alcohols added in the present invention have 2 to 5 carbon atoms and example thereof may include lower alkane diols such as 1,3-butane diol, propylene glycol or ethylene glycol. Especially, the effective rise of cloud point by the addition of the polyhydric alcohol can be remarkably exhibited when the aqueous solution to be measured contains a poor hydrophilic PGE in which the cloud point of the aqueous solution containing such PGE is decreased out of the measurable range even by the addition of a small amount of the salt. The effect of increasing the cloud point by the addition of the polyhydric alcohol, varies depending upon a kind of the polyhydric alcohol added. Consequently, an adequate polyhydric alcohol should be selected in view of the aimed PGE. The concentration of the polyhydric alcohol added to the aqueous PGE solution is in the range of 0 to 100% by weight, preferably 0 to 50% by weight based on the weight of the PGE solution. The concentration of polyhydric alcohol in the present invention is determined by weight of polyhydric alcohol to polyhydric alcohol, and water not including PGE and salt.

The concentration of the aimed PGE is in the range of 0.01 to 50% by weight, preferably 0.1 to 10% by weight, based on the weight of the aqueous PGE solution used for the measurement of the cloud point. If the concentration of the PGE in the aqueous PGE solution is less than 0.01% by weight, it may be difficult to recognize an occurrence of the phase separation. On the other hand, if the concentration of the PGE exceeds 50% by weight, the aqueous PGE solution is too viscous, so that some components remain insoluble in the aqueous PGE solution, whereby it is difficult to measure an accurate cloud point.

The properties of the PGE can be evaluated by using a cloud point profile. Such a cloud point profile is prepared in the following manner. For example, a salt is added to the aqueous PGE solution in various concentrations ranging between 0 to 20% by weight. The cloud point of the aqueous PGE solution is measured at respective concentrations of the salt added. A profile representing a relationship of the cloud points to the respective salt concentration is prepared by use of the measured cloud points.

By comparing the profiles for two different aqueous PGE solutions with each other, it is possible to recognize the difference in properties between the PGEs contained in each solution, which cannot be recognized by a conventional method in which esterification degrees are measured and compared with each other.

Similarly, the comparison between the profiles of various PGEs makes it possible to ascertain the relationship of hydrophilic-lipophilic properties of the PGE. Specifically, in case where the fatty acid moiety of the PGE to be measured, the kind of the salt and/or polyhydric alcohol added and the conditions for the cloud point measurement are identical, the higher the temperature of the cloud point profile is, the higher hydrophilicity the PGE has. This enables determination of the tendency in the hydrophilic and hydrophobic properties of the respective PGEs, so that an adequate PGE can be selected so as to meet the requirements of each application.

In the present invention, by the properties of the PGE produced which is evaluated by the cloud point profile, an influence that the production condition gives to the properties of the PGE can be recognized. Then, it is possible to obtain the aimed PGE having required properties and further to easily achieve a facilitated quality control of the PGE products by changing and selecting the production condition. For instance, an aqueous solution containing PGE produced under given conditions is measured for its cloud point by using a given kind and given concentration of the salt, with or without the addition of polyhydric alcohol, to prepare a cloud point profile therefor. If the thus-prepared cloud point profile deviates to a high temperature side as compared with a profile (reference profile) of an aimed PGE prepared under the same conditions, it is suggested that the PGE prepared has a low average esterification degree, or that there exists an alkali metal salt of fatty acid (fatty acid soap) which is a by-product generated by the reaction of the raw fatty acid and the alkaline catalyst upon the production of the PGE. Accordingly, by adjusting the reaction conditions adequately in the following manner: an amount of the raw fatty acid is increased relative to that of the PG so as to increase the esterification degree of the resultant PGE; an amount of the alkaline catalyst used is controlled to reduce an amount of the soap as a by-product; and an average degree of polymerization is limited to a low level, the cloud point profile of the PGE prepared is caused to approach the reference cloud point profile and the aimed PGE can be obtained.

On the other hand, if the cloud point profile of the PGE is shifted to a low-temperature side as compared with the reference profile, the reaction conditions are varied opposite thereto so as to shift the cloud point profile to a high temperature side, so that the cloud point profile of the PGE products is also caused to approach the reference profile so as to obtain the aimed PGE.

By using the above-mentioned method, it is possible to measure a cloud point of the PGE. The properties of the PGE evaluated by recognizing the difference between the measured and reference profiles, are fed back to the preceding production stage to determine the reaction conditions such as the amount of catalyst used, feed ratio of the PG and fatty acid, the stirring intensity during the reaction, the reaction time, the reaction temperature or the like, whereby the aimed PGE having required properties can be produced. Thus, the process of the present invention is extremely useful for the production of the aimed PGE.

Further, the PGE which has an average esterification degree (a) and is produced from the PG having a given average degree of polymerization by an esterification reaction, cannot be distinguished from a mixture having the same average esterification degree (a) but comprising plural PGEs which are produced from the PG having the same average degree of polymerization but have different average esterification degrees from each other by the usually chemical analyses. However, there is an apparent difference between the cloud points of the single PGE product and the PGE mixture are measured in a particular solution in accordance with the method of the present invention, there exists an apparent difference therebetween, whereby both are clearly distinguished from each other. Further, the cloud point profile thus obtained is applicable to a quality control of the PGE. For example, in case where a blended PGE product is provided by blending the plural PGE products produced under different production conditions, it is important to conduct a quality control of individual PGE products to constantly obtain the blended PGE product having a constant quality. This can be accomplished by preparing a cloud point profile of the PGE products at every production lot to evaluate their qualities. The thus-determined PGE products are then blended together so as to give the blended PGE product whose quality can be determined by using the cloud points profile of the individual PGE products. As a matter of course, by measuring the cloud point of the blended product, a more strict quality control of the blended PGE product can be achieved.

Accordingly, by the present invention, a cloud point of such a complicated PGE composition can be measured in an extremely simplified manner. Since the difference between the properties of various PGEs is clearly recognized by comparing the respective cloud point profiles resulting from the measurement according to the present invention, it is possible to obtain an aimed PGE product having an excellent and constant quality. Thus, the processes of the present invention is useful from a standpoint of the quality control of the PGE.

EXAMPLES

The present invention is described in more detail by way of examples but the examples are only illustrative and not to be construed as limiting the present invention.

Example 1

With various feed molar ratios of fatty acid to PG (hereinafter referred to as "F/P ratio") shown in Table 1, PG having an average degree of polymerization of 10 and stearic acid were fed into a reactor. In addition, a 10% aqueous solution of sodium hydroxide as a catalyst was fed into the reactor in such an amount that the content of the sodium hydroxide was 0.0025% by weight based on the total weight of the raw materials fed. The mixture in the reactor was reacted with each other at 240° C. and normal pressure for 2.5 hours in a nitrogen gas stream. After heated to 260° C., the mixture was further reacted at that temperature for 4 hours so as to give polyglycerol-stearic acid ester.

Aqueous solutions with various salt concentrations shown in Table 1 were prepared and thus-prepared polyglycerol-stearic acid ester was added into the aqueous salt solution to prepare 1% by weight aqueous solution of polyglycerol-stearic acid ester. The resultant solutions were measured for a cloud point. Table 1 shows the cloud point of above-mentioned polyglycerol-stearic acid ester solutions with various salt concentrations and average esterification degrees thereof.

In the foregoing description, for the sake of simplicity, the PGEs produced are alphanumerically represented by using an average degree of polymerization of PG fed, an F/P ratio and a kind of fatty acid charged. For example, if 1 mol of PG having a degree of polymerization of 10 is reacted with 2.0 mol of stearic acid, the resultant polyglycerol-stearic acid ester is represented as "10G2.0S."

In addition, an average esterification degree of PGE produced was determined from amounts of fatty acid and PG which were obtained by saponifying the resultant ester, according to the following equations (1) and (2):

Average esterification degree $$= [(\text{number of moles of fatty acid component})/(\text{number of moles of total hydroxyl groups in PG component})] \times 100 \quad (1)$$

$$= \{(FA/M_{FA})/([(PG_E/M_{PG}) \times (n+2)]\} \times 100 \quad (2)$$

where FA is an amount (g) of fatty acid recovered after saponification of a sample; $M_{FA}$ is a molecular weight of the fatty acid used; $PG_E$ is an amount (g) of PG recovered after saponification of the sample; $M_{PG}$ is an average molecular weight of the PG used ($M_{PG}=74n+18$); and n is an average degree of polymerization of the PG used.

Cloud point profiles of the respective PGEs are shown in Table 1.

TABLE 1

| PGE | F/P ratio | Average esterification degree | Cloud point (°C.) Concentration of salt added (wt %) | | | |
|---|---|---|---|---|---|---|
| | | | 0 | 5 | 10 | 20 |
| 10G2.0S | 2.0 | 24.1 | 90< | 90< | 87.5 | 77.5 |
| 10G2.4S | 2.4 | 25.1 | 90< | 77.5 | 72.5 | 72.5 |
| 10G2.6S | 2.6 | 27.4 | 90< | 67.5 | 57.5 | 67.5 |
| 10G2.8S | 2.8 | 27.2 | 90< | 62.5 | 55> | 55> |
| 10G3.0S | 3.0 | 29.3 | 90< | 55> | 55> | 55> |

As seen from Table 1, the cloud point of the PGE is lowered as the increase of F/P ratio thereof. In addition, as is already known in conventional chemical analysis for esterification rate, it is confirmed that the higher the molar ratio of the raw fatty acid to the raw PG was, the more hydrophobic the resultant PGE became.

Experimental Example

By using the PGE obtained in Example 1, the following simplified emulsification test was conducted. First, compositions Nos. 1 and 2 having feed ratios of respective raw components shown in Table 2 were prepared. After heated to 70° C., each composition was vigorously shaken for 2 minutes by using a shaker (YS-8D manufactured by YAYOI). The composition was allowed to stand at 60° C. for 30 minutes and thereafter observed for an emulsified state thereof. The results of the observation are shown in Table 3 below.

TABLE 2

| Simple Emulsification Test (wt %) | | |
|---|---|---|
| Composition No. | 1 | 2 |
| PGE | 5 | 5 |
| Colza oil | 30 | 30 |
| Sodium chloride | 0.2 | 6.5 |
| | 1% (Note) | 10% (Note) |
| 10% aqueous solution of acetic acid | 2 | 2 |
| Water | balance | balance |
| Total | 100 | 100 |

Note: concentration based on the weight of the aqueous phase.

TABLE 3

| PGE product | Composition No. 1 | Composition No. 2 |
|---|---|---|
| 10G2.0S | C | C |
| 10G2.4S | B | B |
| 10G2.6S | B | A |
| 10G2.8S | A | D |
| 10G3.0S | D | D |

Note: Observation results of emulsification tests are ranked as follows.
A: homogeneously emulsified;
B: water-release percentage is not more than 20%;
C: water-release percentage is more than 20% but less than 40%; and
D: water-release percentage is not less than 40%.

As seen from Table 3, the emulsified state of the PGE appeared differently when the F/P ratio upon the synthesis thereof was slightly changed. Thus, a difference in property and quality between these PGEs was clearly indicated by the cloud point profiles thereof.

In the emulsification test of the composition No. 1, the PGE 10G2.8S was superior in an emulsified state to the PGE 10G2.6S. However, as seen from the cloud point profiles shown in Table 1, the PGE 10G2.8S had substantially only one measurable cloud point. Consequently, the use of the PGE 10G2.8S profile as a reference profile makes it difficult to evaluate property and quality of various PGEs. Then, the measurement of cloud points was conducted again by adding polyhydric alcohol to the aqueous solution of PGE 10G2.8S, to prepare another cloud point profile thereof.

The cloud points of the prepared solutions in which the concentrations of PGE and propylene glycol are 1% and 15%, respectively, are measured with various sodium chloride concentration. The results are shown in Table 4.

TABLE 4

| PGE product | Cloud point (°C.) Concentration of salt (wt %) | | | |
|---|---|---|---|---|
| | 0 | 5 | 10 | 20 |
| 10G2.8S | 90< | 72.5 | 67.5 | 62.5 |

The solution to which sodium chloride only was added could not provide a suitable cloud point profile. On the other hand, as seen from Table 4, the cloud point profile of the PGE solution to which propylene glycol was added, was suitably varied in proportion to the change in concentration of sodium chloride.

By using this cloud point profile, it was easily determined that the PGEs having slightly different molar ratios showed considerably different emulsifiabilities. Conventionally, it has been considered that these PGEs have the same properties, That is, these PGEs cannot be distinguished from each other by conventional analyzing methods. In addition, when the results of the evaluation conducted by using the cloud point profile are fed back to the PGE production, the conditions therefor can be advantageously adjusted to obtain the aimed PGE. For example, in case it is intended to obtain the PGE exhibiting a high emulsifiability under a high salt concentration condition, the aimed PGE can be produced by using the cloud point profile of the PGE 10G2.6S as a reference cloud point profile. Specifically, the production conditions of the PGE is adjusted such that a cloud point profile of PGE to be produced approaches the reference cloud point profile as close as possible. This procedure makes it possible to selectively produce the aimed PGE.

Example 2

With the F/P ratios shown in Table 5, PG having an average degree of polymerization of 10 and lauric acid were charged into a reactor. In addition, a 10% aqueous solution of sodium hydroxide as a catalyst was fed into the reactor such that the content of the sodium hydroxide was 0.0025% by weight based on the total weight of the raw materials fed. The mixture in the reactor was reacted with each other at 240° C. for 2.5 hours under atmospheric pressure in a nitrogen gas stream. After heated to 260° C., the mixture was further reacted at that temperature for 4 hours so as to give polyglycerol-lauric acid ester.

TABLE 5

| Production Conditions of Polyglycerol-Lauric Acid Ester | | |
|---|---|---|
| PGE product | F/P ratio | Average esterification degree |
| 10G0.7L | 0.7 | 17.4 |
| 10G1.0L | 1.0 | 17.9 |
| 10G1.5L | 1.5 | 20.4 |
| 10G2.0L | 2.0 | 22.6 |
| 10G3.0L | 3.0 | 27.8 |
| 10G5.0L | 5.0 | 40.7 |

The thus-prepared polyglycerol-lauric acid esters were melted at 80° C. and blended at the weight ratios shown in Table 6 to obtain blended products Nos. 1 to 3 each having an average esterification degree corresponding to that of PGE 10G3.0L.

The thus-obtained blended products of the polyglycerol-lauric acid esters were dissolved in aqueous sodium chloride solution to prepare an aqueous solution containing 5% of polyglycerol-lauric acid ester. The resultant solutions were measured for their cloud points in the same manner as described above. The cloud point profiles shown in Table 6 were obtained.

a result, the cloud point profiles as shown in Table 7 were obtained. The reason why sodium sulfate was used instead of sodium chloride was such that the cloud points of all the PGEs measured in the presence of sodium chloride were 90° C. or higher, thereby resulting in inaccurate measurements.

Next, 10 parts by weight of an oil-soluble substance composed of 2-ethyl-hexanoic acid triglyceride produced by Nisshin Seiyu K.K. was added to 90 parts by weight of each PGE to prepare a mixture. The mixture was heated at a temperature of 60° to 70° C. while stirring. The 0.5 g of the mixture was diluted with 100 ml of an aqueous solution of citric acid of pH 3 to conduct a solubilization test for the oil-soluble substance. The results of the test are also shown in Table 7.

TABLE 7

| PGE product | Concentration of sodium sulfate (wt % based on solvent) | | | | | | | Solubilization Test |
|---|---|---|---|---|---|---|---|---|
| | 0 | 3.5 | 5 | 8.5 | 10 | 12.5 | 20 | |
| 10G0.7L | — | — | — | — | 90< | 57.5 | 30> | A |
| 10G1.0L | — | — | 90< | 62.5 | 47.5 | — | 30> | A |
| 10G1.5L | 90< | 52.5 | 42.5 | — | 30> | — | 30> | B |

In Table 7, the solubilization of the PGE products was evaluated with the following ratings:

A: homogeneously solubilized;
B: Precipitated from heterogeneous mixture.

In addition, the method of the present invention was able to be used for measuring cloud points of PGEs having a high hydrophilicity. Consequently, the cloud point profiles obtained from the measurement were useful for evaluating properties or qualities of different PGE products. Accordingly, when the cloud point profile of the PGE evaluated as good in the above solubilization test was used as a reference cloud point profile, PGEs having a high solubilizability could be selectively produced.

TABLE 6

| PGE product | Mixing ratio (wt %) | | | | | Average esterification degree | Cloud point (°C.) Concentration of salt added (wt %) | | | |
|---|---|---|---|---|---|---|---|---|---|---|
| | 10G1.0L | 10G1.5L | 10G2.0L | 10G3.0L | 10G5.0L | | 0 | 5 | 10 | 20 |
| 10G3.0L | — | — | — | 100 | — | 27.8 | 80 | 67.5 | 60.0 | 45.0 |
| Blend 1 | 71.8 | — | — | — | 28.2 | 28.0 | 90< | 90< | 90< | 77.5 |
| Blend 2 | — | 71.0 | — | — | 29.0 | 27.9 | 90< | 90< | 90.0 | 65.0 |
| Blend 3 | — | — | 75.1 | — | 24.9 | 27.9 | 90< | 90.0 | 72.5 | 57.5 |

When the PGE 10G3.0L and the blended products Nos. 1 to 3 were analyzed for their esterification degrees by using conventional methods, these PGEs exhibited similar average esterification degrees and therefore could not be distinguished from one another. On the other hand, when measured for their cloud points by using the process of the present invention, these PGEs could be clearly distinguished from each other so that differences in physical properties or qualities between the blended products could be determined properly.

Next, the PGE 10G0.7L, the PGE 10G1.0L and the PGE 10G1.5L shown in Table 5 above were respectively dissolved in aqueous sodium sulfate solution to prepare a 5% PGE solution. The PGE aqueous solution was then measured for the cloud points by changing the concentration of sodium sulfate contained therein variously as shown in Table 7. As

Example 3

Example 1 was repeated in the same manner as described except that the concentration of the alkaline catalyst in the reaction system, namely the amount of the 10% sodium chloride solution added, was changed as shown in Table 8 while the F/P ratio was kept at 2.4.

TABLE 8

| PGE product | Amount of catalyst used (wt %) | Average esterification degree (%) |
|---|---|---|
| (a) 10G2.4S | 0.0025 | 25.1 |
| (b) 10G2.4S | 0.125 | 25.4 |

The thus-obtained polyglycerol-stearic acid esters (a) and (b) were dissolved in aqueous sodium chloride solution with various concentration shown in Table 9 to prepare an aqueous solution containing 1% of polyglycerol-stearic acid ester. The cloud point of each solution was measured and the results are shown in Table 9.

TABLE 9

| PGE product | Cloud point (°C.) Concentration of salt added (wt %) | | | |
| --- | --- | --- | --- | --- |
| | 0 | 5 | 10 | 20 |
| (a) 10G2.4S | 90< | 67.5 | 62.5 | 55> |
| (b) 10G2.4S | 90< | 87.5 | 77.5 | 62.5 |

When the PGEs (a) and (b) were measured for their esterification degrees using conventional methods, it could not be determined that the esterification degrees of the PGE were adversely affected by the co-existing metal salt of the fatty acid (byproduct soap derived from the catalyst). On the other hand, when the cloud point profile prepared according to the process of the present invention was used for the evaluation of properties of these PGES, it could be clearly recognized that the PGE (b) had a higher hydrophilic property than the PGE (a).

That is, even when the different amounts of the catalyst are used in the PGE production, the properties and qualities of the PGE can be easily distinguished from each other by using the process of to the present invention, whereby the PGE having a constant property and quality can be produced.

What is claimed is:

1. A process of making a cloud point profile of polyglycerol-fatty-acid ester, which is produced by reacting a fatty acid with polyglycerol at a feed molar ratio of the fatty acid to the polyglycerol of not more than 5, comprising:

(a) adding polyglycerol-fatty acid ester to an aqueous solution of a salt, polyhydric alcohol, or a mixture thereof to prepare a homogeneous aqueous polyglycerol-fatty acid ester solution;

(b) heating the obtained homogeneous aqueous solution to allow to change the homogenous aqueous solution into a heterogeneous aqueous polyglycerol-fatty acid ester solution;

(c) measuring a temperature at which the homogeneous aqueous solution changes into a heterogenous aqueous solution as a cloud point at the concentration of a salt, polyhydric alcohol or a mixture thereof;

(d) repeating the above-procedure from (a) to (c) at different concentrations of a salt, polyhydric alcohol or a mixture thereof; and (e) making a cloud point profile indicating a relationship in the range of each measured cloud point and the concentration of a salt, the polyhydric alcohol or a mixture thereof.

2. A process of evaluating polyglycerol-fatty acid ester properties, said polyglycerol-fatty acid ester being produced by reacting a fatty acid with polyglycerol at a feed molar ratio of the fatty acid to the polyglycerol of not more than 5, comprising:

preparing a cloud point profile of a first polyglycerol-fatty acid ester having required properties as a reference profile, said profile being made according to the method defined in claim 1;

measuring a cloud point of a second polyglycerol-fatty acid ester which properties are unknown and said cloud point being measured at a measuring condition according to the procedure of (a) to (c) defined in claim 1;

comparing said reference profile with said cloud point of a second polyglycerol-fatty acid ester at same measuring condition to determine the difference in properties between the two polyglycerol-fatty acid ester; and evaluating properties of said second polyglycerol-fatty acid ester based on deviation of said cloud point from said reference profile.

3. A process for the preparation of polyglycerol-fatty acid ester, which is produced by reacting a fatty acid with polyglycerol at a feed molar ratio of the fatty acid to the polyglycerol of not more than 5, comprising:

preparing a cloud point profile of a first polyglycerol-fatty acid ester which properties are known as a first reference profile, said profile being made according to the method defined in claim 1;

preparing a second cloud point profile of a second polyglycerol-fatty acid ester produced under the same reaction conditions of the first polyglycerol-fatty acid ester, said second profile being made according to the method defined in claim 1;

comparing said second profile with said first reference profile and selecting reaction conditions for the production of a polyglycerol-fatty acid ester having the same properties as the first polyglycerol-fatty acid ester of the reference profile; and adjusting reaction conditions to said selected conditions and producing a polyglycerol-fatty acid ester.

4. A process for the preparation of polyglycerol-fatty acid ester, which is produced by reacting a fatty acid with polyglycerol at a feed molar ratio of the fatty acid to the polyglycerol of not more than 5, comprising:

preparing a cloud point profile of a first polyglycerol-fatty acid ester having required properties as a reference profile, said profile being made according to the method defined in claim 1;

measuring a cloud point of a second polyglycerol-fatty acid ester produced under one reaction condition, said cloud point being measured at a measuring condition according to the procedure of (a) to (c) defined in claim 1;

comparing said second cloud point with said reference profile at same measuring condition and selecting reaction conditions for the production of polyglycerol-fatty acid ester having the same properties as the first polyglycerol-fatty acid ester of the reference profile; and adjusting reaction conditions to said selected conditions and producing a polyglycerol-fatty acid ester.

5. A process according to claim 1, wherein said polyglycerol-fatty acid ester contains a polyglycerol moiety having an average degree of polymerization of not less than 4 to 30.

6. A process according to claim 1, wherein said polyglycerol-fatty acid ester contains a polyglycerol moiety having an average degree of polymerization of 4 to 20.

7. A process according to claim 1, wherein said polyglycerol-fatty acid ester contains a polyglycerol moiety having an average degree of polymerization of 6 to 12.

8. A process according to claim 1, wherein the fatty acid as a raw material of said polyglycerol-fatty acid ester is linear or branched, saturated or unsaturated $C_6$–$C_{22}$ fatty acid or $C_6$–$C_{22}$ hydroxy-substituted fatty acid.

9. A process according to claim 1, wherein the concentration of said polyglycerol-fatty acid ester in said homogeneous aqueous solution is 0.01 to 50% by weight.

10. A process according to claim 1, wherein the concentration of said polyglycerol-fatty acid ester in said homogeneous aqueous solution is 0.1 to 10% by weight.

11. A process according to claim 1, wherein said salt is an inorganic salt.

12. A process according to claim 1, wherein said salt an alkali metal salt.

13. A process according to claim 1, wherein said cloud point is measured at a temperature of 0° to 100° C.

14. A process according to claim 1, wherein said polyhydric alcohol has 1 to 5 carbon atoms.

15. A process according to claim 1, wherein the amount of said salt added is in the range of 0 to 50% by weight, based on the weight of salts to total weight of salts, polyhydric alcohol and water not including polyglycerol-fatty acid ester, and the amount of said polyhydric alcohol added is in the range of 0 to 100% by weight, based on the weight of polyhydric alcohol to polyhydric alcohol and water not including polyglycerol-fatty acid ester.

16. A process according to claim 2, wherein said first polyglycerol-fatty acid ester is a single kind of polyglycerol-fatty acid ester and said second polyglycerol-fatty acid ester is a mixture of not less than two kinds of polyglycerol-fatty acid esters which are produced under different conditions.

17. A process according to claim 2, wherein each of said first polyglycerol-fatty acid ester and said second polyglycerol-fatty acid ester is a mixture of not less than two kinds of polyglycerol-fatty acid esters which are produced under different conditions.

18. A process according to claim 2, wherein said cloud points are measured at a temperature of 0° to 100° C.

19. The method according to claim 3, wherein said reaction conditions include at least one of the feed molar ratio of fatty acid to polyglycerol, the amount of catalyst, the agitation intensity, the reaction time and the reaction temperature.

20. The method according to claim 3, wherein said cloud points are measured at a temperature of 0° to 100° C.

21. The method according to claim 4, wherein said reaction conditions include at least one of the feed molar ratio of fatty acid to polyglycerol, the amount of catalyst, the agitation intensity, the reaction time and the reaction temperature.

22. The method according to claim 4, wherein said cloud points are measured at a temperature of 0° to 100° C.

* * * * *